United States Patent [19]

Green et al.

[11] Patent Number: 5,013,350

[45] Date of Patent: May 7, 1991

[54] STABILIZED THIOCARBONATE SOLUTIONS

[75] Inventors: James A. Green, Chino; Donald C. Young, Fullerton, both of Calif.

[73] Assignee: Union Oil Company of California, Los Angeles, Calif.

[21] Appl. No.: 55,923

[22] Filed: May 29, 1987

Related U.S. Application Data

[60] Division of Ser. No. 490,461, May 2, 1983, abandoned, which is a continuation-in-part of Ser. No. 315,492, Oct. 27, 1981, Pat. No. 4,476,113.

[51] Int. Cl.$^5$ .................... A01N 59/02; A01N 47/28
[52] U.S. Cl. ............................ 71/65; 71/3; 71/4; 71/119
[58] Field of Search ................... 71/65, 3, 4

[56] References Cited

U.S. PATENT DOCUMENTS

| | | | |
|---|---|---|---|
| 1,044,452 | 11/1912 | Halland . | |
| 2,046,128 | 6/1936 | McQuiston | 424/121 |
| 2,676,129 | 4/1954 | Bashour | 514/512 |
| 2,731,487 | 1/1956 | Bashour | 558/243 |
| 2,836,532 | 5/1958 | Seifter | 424/703 |
| 2,836,533 | 5/1958 | Seifter | 167/14 |
| 3,133,857 | 5/1964 | Swezey | 514/746 |
| 3,837,304 | 9/1974 | Carroll | 111/6 |
| 3,892,741 | 7/1975 | Taylor | 260/246 B |
| 4,042,501 | 8/1977 | King | 210/737 |
| 4,078,912 | 3/1978 | Hawkins | 71/28 |
| 4,435,304 | 3/1984 | Lindstrom et al. | 252/156 |
| 4,476,113 | 10/1984 | Young et al. | 424/161 |
| 4,551,167 | 11/1985 | Young et al. | 71/64.1 |
| 4,726,144 | 2/1988 | Young et al. | 47/58 |

FOREIGN PATENT DOCUMENTS 1501516 2/1978 United Kingdom .

OTHER PUBLICATIONS

Yeaman, J. Chem. Soc. Trans., vol. 119, (1921), pp. 38-54.

J. Sci. Fd. Agric., 1977, 28, 673-683, Inhibition of Nitrification of Nitrapyrin, Carbon Disulphide and Trithiocarbonate, by John Ashworth, Geoffrey G. Briggs, Avis A. Evans and Jiri Matula.

Agricultural Chemicals-Book III, Miscellaneous Chemicals, 1976-1977 Revision, W. R. Thomson Publications, P.O. Box 7964, Fresno, CA, (1976), pp. 11-12.
Agricultural Chemicals-Book IV, Fungicides, 1976-1977 Revision, W. R. Thomson, Thomson Publications, P.O. Box 7964, Fresno, CA (1976), pp. 15-16.

O'Donoghue and Kahan, "Thiocarbonic Acid and Some of Its Salts," Journal of the Chemical Society, vol. 89 (II), pp. 1812-1818 (1906).

Mills and Robinson, "Ammonium Polysulphides, Hydrogen Pentasulphide, and the Thiocarbonic Acids," Journal of the Chemical Society, vol. 1928 (II), pp. 2326-2332.

"The Soil Pest Complex," Agricultural and Food Chemistry, vol. 3, pp. 202-205, (1955).

Soil Biology and Biochemistry, J. M. Bremner and L. G. Bundy, vol. 6, pp. 161-165 (1974).

Chemistry and Industry, J. Ashworth et al., Sep. 6, 1975, pp. 749-750.

C. R. Acad. Sc. Paris, t276, (Mar. 12, 1973), pp. 951-954, Zins et al.

Chemical Abstracts, vol. 87, 1977, No. 87:16857s. "Effect of Pyridine, Toluene and Carbon Disulfide on the Growth of Nitrifying Bacteria in Omeliansky's Medium".

Chemical Abstracts, vol. 99, 1983, No. 99:138732r, "Effect of a Carbon Disulfide Emulsion on the Nitrification Capacity Soil," Yanover et al.

*Primary Examiner*—Glennon H. Hollrah
*Assistant Examiner*—Brian G. Bembenick
*Attorney, Agent, or Firm*—Gregory F. Wirzbicki; Michael H. Laird

[57] ABSTRACT

Fumigation to control bacteria, fungi, insects, rodents, nematodes and weeds is accomplished by decomposing a compound represented by the formula $$MCS_x$$

wherein M is selected from the group consisting of alkaline earth metal cations and X varies from 3 to 4, to yield carbon disulfide.

This invention also provides a composition useful for fumigating soil and providing plant nutrients, which composition comprises the above compound (or an alkali metal thiocarbonate) in combination with a source of nitrogen, e.g. urea, ammonium nitrate, etc.

Calcium thiocarbonates, i.e., $CaCS_3$ and $CaCS_4$ are claimed as novel compounds.

22 Claims, No Drawings

STABILIZED THIOCARBONATE SOLUTIONS

RELATED APPLICATIONS

This application is a divisional application of our co-pending application Ser. No. 490,461 filed May 2, 1983, for METHOD OF FUMIGATION (now abandoned), which was a continuation in part of Ser. No. 06/315492 filed 10/27/81 (Now U.S. Pat. No. 4,476,113).

BACKGROUND OF THE INVENTION

1. Field of the Invention

This invention relates to a method for controlling fungi, insects, rodents, nematodes and weeds, and for inhibiting nitrification in a soil environment.

2. Description of the Art

Among the more economically serious plant parasites are nematodes, roundworms comprising as many as 10,000 species, of which at least 150 are known to adversely affect plant life. Plant parasitic nematodes have been known since about 1750. Most of the nematodes which cause crop damage do so by feeding on plant roots and, therefore, are found primarily in the upper few inches of soil in the roots or in close proximity to the roots. Nematode feeding causes hypertrophy or gall formation, and the evidence of heavy infestation is plant stunting, pale foliage, wilting, and even plant death in extreme cases.

Virtually all of the world's crops and ornamental plants can be attacked by parasitic nematodes. Important destructive nematode species include the root knot nematodes, which are hosted by tomatoes, alfalfa, cotton, corn, potatoes, citrus and many other crops, the golden nematode of potatoes, the sugar beet cyst nematode and the citrus nematode. These, and a few other species, are described in "The Soil Pest Complex", *Agricultural and Food Chemistry*, Vol. 3 pages 2205 (1955). Also described therein is a further complication resulting from nematode infestation, namely, a lowered resistance to the effects of plant attack by bacteria and pathogenic soil fungi.

Except for small volumes of soil which can be sterilized, it has not been found possible to eliminate nematodes. Parasite populations can, however, be kept at levels which economically permit agricultural operations by soil fumigation, crop rotation using nonhosting plant varieties, and (to a much lesser extent) the development of plants which are resistant to infestation. In many instances, control of nematodes is achieved only by combinations of these techniques, and most control programs have proven quite costly.

The process of soil fumigation requires the movement of gaseous chemicals through the soil which is treated, and the readily apparent necessity for a sufficient concentration of gas at a given temperature and pressure condition to be lethal to the pest which would be controlled. Volatility of the chemical agent is critical to successful fumigation, since a very volatile substance will disperse too readily and not develop an effective concentration except for locations very close to the point of introduction to the soil. Substances having a very low volatility are also undesirable, since they will not disperse in the soil, and will be effective only at locations near the point of introduction.

Carbon disulfide is the first reported soil fumigant, used in Europe during the 1870's to control the sugar beet nematode. This agent is commercially impractical, however, since very large quantities must be applied (due to the high volatility) and the material is quite flammable, reportedly being ignited even by static electricity resulting from pouring the material out of drums. In addition, carbon disulfide possesses a very objectional odor, and its vapors are toxic to humans. When sold for fumigant use, the carbon disulfide is normally mixed with an inert fire retarding compound, such as carbon tetrachloride, and occasionally also with another fumigant. Typically, these compositions do not contain over about 20 percent by weight of carbon disulfide.

In addition to soil uses, carbon disulfide has been proven effective in the fumigation of commodities, as an insecticide, as a rodenticide, and for controlling certain weeds. W. T. Thomson, in *Agricultural Chemicals Book III Miscellaneous Chemicals*, 1976-77 Revision (Thomson Publications, P.O. Box 7964, Fresno, CA), describes application methods to grain entering storage and to stored grains, and the chamber fumigation of commodities, at pages 1112. Examples are also given of methods for controlling apple tree borers and soil living rodents.

Carbon disulfide is approved by the U.S. Environmental Protection Agency as an insecticide, when used as a fumigant after harvest for barley, corn, oats, popcorn, rice, rye, sorghum (milo), and wheat. Carbon disulfide is also useful as a nematocide for other preplanted (fallow) soil. The amount of carbon disulfide, recommended for this use, would be phytotoxic if applied to growing plants.

Numerous compositions possessing nematocidal properties have been developed, including active ingredients such as the polyamines of U.S. Pat. No. 2,979,434 to Santmyer, the heterocyclic compounds of U.S. Pat. No. 2,086,907 to Hessel, and various halogenated compounds. Among the useful halogen-containing nematocides are 1,2-dibromoethane, methyl bromide, 3-bromopropyne, 1,2-dichloropropane, ethylene dichloride and others, all of which are quite phytotoxic, therefore restricting their utility to mostly preplanting treatments.

One compound which enjoyed considerable commercial success is 1,2-dibromo-3-chloropropane (DBCP), which can be used to control nematodes in soils with growing perennial plants. However, use of this material has been limited due to a finding of undesirable reproductive system effects in workers exposed to the chemical, and the possibility that the compound is a carcinogen. The unavailability of DBCP has been a serious setback to growers of perennial crops, such as grapes, stone fruits and nuts, since these crops experience more severe cumulative nematode population increases, and most replacement soil fumigants are phytotoxic. U.S. Patents concerned with the use of DBCP as a soil fumigant include U.S. Pat. No. 2,937,936 to Schmidt and U.S. Pat. No. 3,049,472 to Swezey.

A further class of materials which have been utilized to control nematodes is the thiocarbonates. U.S. Pat. No. 2,676,129 to Bashour describes the preparation of lower aliphatic disubstituted trithiocarbonates having the structure as in (1):

wherein $R_1$ and $R_2$ are alkyl radicals having from three to nine carbon atoms. The compounds were dissolved in acetone and added to nematode-infested soils, resulting in control of the nematodes.

Other compounds have been reported by Seifter in U.S. Pat. Nos. 2,836,532 and 2,836,533, the former relating to the use of sodium and potassium trithiocarbonate, and the latter pertaining to alkali metal and ammonium salts of tetrathioperoxycarbonic acid. Both are described as effective in nematode control.

These references state that "not all carbon disulfide derivatives are effective nematode toxicants." Furthermore U.S. Pat. No. 2,836,532 points out that sodium trithiocarbonate is unexpectedly superior to potassium trithiocarbonate as a nematocide.

Another serious problem in agriculture is that of low nitrogen use-efficiency, since crops have been found to recover only 30 to 70 percent of the total amount of expensive fertilizer nitrogen which is applied to the soil. Most of the lost nitrogen is due to nitrite and nitrate ions, which are exceptionally mobile in a soil environment, and therefore are readily lost by surface runoff and also by leaching from the plant root zone into deeper soil. Other losses of these ions are due to denitrification, which is reduction to elemental nitrogen or gaseous nitrogen oxides under conditions of limited aeration. In addition to the direct economic losses, these nitrogen forms constitute environmental pollutants when runoff enters surface and ground water systems.

Although some nitrogen is applied to soil in the form of nitrate (e.g., ammonium nitrate-containing fertilizers), most nitrogen fertilization is with ammonia, ammonium compounds other than nitrate and urea materials. Ammonium nitrogen is fairly tightly bound by various physical and chemical processes in a soil environment and, therefore, is much less subject to losses. Unfortunately, the bound ammonium nitrogen is also less available to plants.

The process of nitrification results in conversion of ammonium ions into nitrate ions. Microbial species known as nitrosomonas oxidize ammonium to nitrate; nitrobacter species oxidize nitrite to nitrate. This more mobile ion is easily taken up by plant roots and is also readily assimilated by plants. In this regard, the nitrification process is desirable, but control of the rate at which conversion occurs has not been easily obtained. Inhibition of the nitrification would tend to make the applied nitrogen available to plants over a longer period of time, resulting in an increased plant uptake efficiency.

Various compositions have been offered as inhibitors of nitrification, including expensive organic materials such as 2-chloro-6-(trichloromethyl)-pyridine, 2-amino-4-chloro-6-methyl-pyrimidine, sulfathiazole, alkanolysulfathiazoles, and others. A paper by J. M. Bremner and L. G. Bundy in *Soil Biology and Biochemistry*, Vol. 6, pages 161165 (1974) describes the efficacy of various volatile organic sulfur compounds, including methyl mercaptan, dimethyl sulfide, dimethyl disulfide, carbon disulfide, and hydrogen sulfide. Carbon disulfide in very small amounts is described as having "a remarkable inhibitory effect on nitrification of ammonium in soils incubated in closed systems". Carbon disulfide was tested in the field by J. Ashworth et al., *Chemistry and Industry*, Sept. 6, 1975, pages 749-750, and found to be effective as a nitrification inhibitor. Hawkins, in U.S. Pat. No. 4,078,912, describes the use of sodium, potassium and ammonium trithiocarbonates, and of xanthates, either alone or in fertilizer mixtures, to inhibit nitrification; the mode of operation is attributed to a release of carbon disulfide by the compounds.

One additional potential problem, which could be presented to the agricultural industry in the very near future, is the loss of the widely used, effective fumigant, 1,2-dibromoethane, due to environmental concerns. This agent is approved for use on the same crops as is carbon disulfide, and is additionally used extensively in chambers for fumigating fruits and vegetables to control various insects.

The chemistry of thiocarbonic acids and salts has been studied in some detail, as indicated in the papers by O'Donoghue and Kahan, *Journal of the Chemical Society*, Vol. 89 (II), pages 1812-1818 (1906); Yeoman, *Journal of the Chemical Society*, Vol. 119, pages 38-54 (1921); and Mills and Robinson, *Journal of the Chemical Society*, Vol. 1928 (II), pages 2326-2332 (1928). According to O'Donoghue and Kahan, derivatives of thiocarbonic acid were prepared by Berzelius, who reacted aqueous solutions of hydrosulfides with carbon disulfide, the reactions occurring as in (2):

$$2\ KHS + CS_2 \rightarrow K_2CS_3 + H_2S \qquad (2)$$

giving unstable solutions which yielded unstable crystalline salts.

Other thiocarbonates were prepared and further characterized by O'Donoghue and Kahan. Their paper, at page 1818, reports the formation of ammonium thiocarbonate by reacting liquid ammonia with cold alcoholic thiocarbonic acid, prepared by dropping a ·lution of 'calcium thiocarbonate' into concentrate. ·y-drochloric acid. The 'calcium thiocarbonate' obtained by the authors is reported to be a double salt, including the calcium cation in combination with both hydroxide and trithiocarbonate anions.

The noted paper by Yeoman reports the further study of thiocarbonates (called trithiocarbonates therein) and also reports the preparation and properties of perthiocarbonates (or tetrathiocarbonates), derivatives of tetrathiocarbonic acid, $H_2CS_4$. Yeoman prepared various thiocarbonate salts including alkali metal and alkaline earth metal tri- and tetrathiocarbonates, as well as the ammonium salts. It is noted by Yeoman that the ammonium thiocarbonates are very unstable, which would argue against their use as fumigants.

Considerable explanation is provided concerning the stability of the other thiocarbonates, with the alkali metal thiocarbonates exemplified by sodium and potassium trithiocarbonates and perthiocarbonates. Sodium trithiocarbonate solutions in water are said to remain stable only if oxygen and carbon dioxide are "rigidly excluded"; the presence of oxygen causes decomposition to form carbon disulfide and thiosulfates, while carbon dioxide decomposes the solution to give a carbonate and carbon disulfide. Similarly, solutions of sodium perthiocarbonate are reported to be stable for a considerable time in the absence of oxygen, the presence of air causing decomposition into thiosulfate and carbon disulfide, while carbon dioxide decomposes the compound to form a carbonate, elemental sulfur, carbon disulfide, and hydrogen sulfide. The potassium thiocarbonates behave similarly, according to Yeomans.

Yeomans also attempted to prepare and characterize for stability thiocarbonate salts of four of the alkaline earth metals. Yeomans was unable to prepare a "pure" calcium tri- or tetrathiocarbonate, but observed that the double salt of calcium trithiocarbonate that he prepared was more stable (probably because it was less hygroscopic) than the sodium or potassium thiocarbonates. The Barium tetrathiocarbonate could not be isolated (although Yeomans felt that it existed in solution). Barium trithiocarbonate was found to be stable although it was alleged to behave like sodium trithiocarbonate when dissolved in water. The preparation of aqueous solutions of the tri- and tetrathiocarbonate of magnesium and strontium was alleged (the magnesium thiocarbonates were not characterized), however the stability of any of the magnesium or strontium salts or solutions was not determined.

In view of the above, it is clear that the chemical behavior of the alkaline earth metal thiocarbonate salts is unpredictable. Moreover, it is clear that there is no method taught in the art for preparing either the trithioor tetra thio-salt of calcium.

A need exists for a fluid which can release carbon disulfide for fumigation and nitrification inhibiting purposes, but which can be stored and handled safely and without significant loss of effectiveness during a reasonable commercial storage and delivery cycle.

It is therefore an object of the present invention to provide a stabilized liquid composition which can be caused to release fumigants, including carbon disulfide.

It is a further object to provide a stabilized composition which is miscible with water to form a fumigant and nitrification inhibitor which can be applied to soils by means of fluid handling equipment or introduced into irrigation water.

Other objects and advantages of the instant invention will be apparent from a careful reading of the specification below.

SUMMARY OF THE INVENTION

This invention is a method for providing a fumigant to a space to control bacteria, fungi, insects, rodents, nematodes and weeds which comprises decomposing, in said space, a compound represented by the formula:

$$MCS_x$$

wherein M is selected from the group consisting of alkaline earth metal cations and S varies from 3 to 4, to yield carbon disulfide. The instant method may be used to fumigate soil to control nematodes. This invention also provides novel calcium thiocarbonates, i.e. $CaCS_3$ and $CaCS_4$ which are useful for fumigating soil and fumigating compositions that are useful in providing plant nutrients, which fumigating compositions comprises compounds prepresented by above formula (or an alkali metal thiocarbonate) in combination with a source of nitrogen, e.g. urea, ammonium nitrate, etc.

DESCRIPTION OF THE INVENTION

It has been unexpectedly discovered that the alkaline earth metal thiocarbonates are efficient fumigants and are surprisingly more stable to loss of the active fumigating moiety, carbon disulfide, upon storage as an aqueous solution, than the analogous ammonium and alkali metal thiocarbonates. Moreover, the alkaline earth metal thiocarbonates do not form ammonium thiocyanate upon storage and therefore are not phytotoxic to plants when used in effective fumigating concentrations.

The novel calcium thiocarbonates are preferred for use in the method of this invention, due to their storage stability. Calcium tetrathiocarbonate is the most preferred alkaline earth metal thiocarbonate for use in the method of the present invention, due to the storage stability of aqueous solutions thereof.

The alkaline earth metal thiocarbonates used as fumigants in the method of the present invention may be prepared by reacting an alkaline earth metal sulfide, or a mixture of an alkaline earth metal sulfide and sulfur, with carbon disulfide, at conditions sufficient to produce the alkaline earth metal trithiocarbonate or the alkaline earth metal tetrathiocarbonate, respectively. Preferably, the reaction takes place in an aqueous solution to provide the aqueous fumigant composition directly. Any sulfur required may be dispersed in said aqueous solution. The alkaline earth metal sulfide may be generated in-situ by contacting an aqueous solution, containing a solubilized or dispersed precursor of said alkaline earth metal sulfide (e.g., an alkaline earth metal salt, oxide or hydroxide) with hydrogen sulfide, either prior to or simultaneously with the carbon disulfide.

The reaction may be carried out at a temperature of from 0° C. to the boiling point of carbon disulfide, and preferably from about 15° C. to about 35° C. for convenience. The reaction is preferably carried out under an inert or reducing gas atmosphere to avoid oxidation of any of the sulfur compounds to sulfur oxide moeities such as thiosulfate. The reactants are preferably provided in essentially stoichiometric amounts corresponding to one mole of alkaline earth metal sulfide to one mole of carbon disulfide for the alkaline earth metal trithiocarbonate and a mole of sulfur, in addition, for the alkaline earth metal tetrathiocarbonate. The concentration of alkaline earth metal trithiocarbonate usually varies from 0.01 to 55 percent, by weight, in the aqueous reaction solution, while the alkaline earth metal tetrathiocarbonate usually varies from 0.01 to 45 percent, by weight. Preferably, the concentration of the aqueous solution of the alkaline earth metal thiocarbonates will not exceed about 33 percent, by weight, to avoid precipitation at low temperatures. The salt may be recovered from the aqueous solution by evaporation of the water and filtration of the resulting precipitate (under an inert or reducing atmosphere) if it is desirable to store the alkaline earth metal thiocarbonate for extremely long periods prior to use as a fumigant; however, the aqueous solution is substantially stable in and of itself therefore there is usually no need to recover the salt as a substantially anhydrous solid. Moreover, it is generally easier to handle the liquid solution than the solid alkaline earth metal thiocarbonate.

While the above described alkaline earth metal thiocarbonates are the active fumigants and therefore may be used in any form (e.g., as a powder admixed with inert solids, as solution or dispersion in an organic solvent, etc.), it is preferred to use the above aqueous solutions directly as fumigants. Therefore, the method of the invention may be carried out by the application of aqueous solutions of alkaline earth metal thiocarbonates.

The above aqueous reaction solutions may be diluted prior to application to provide a solution concentration of as low as 0.01 percent by weight of the alkaline earth metal thiocarbonate. The aqueous solution may incorporate surfactants to assist in application as a fumigant. Preferably, a strong base, e.g., an alkali metal hydroxide such as sodium hydroxide is added to the aqueous solution of alkaline earth metal thiocarbonate to increase the stability thereof during application. The invention also involves an aqueous solution of alkali metal and alkali earth metal thiocarbonates of increased stability obtained by adjusting the pH of the solution to at least 7, preferably at least 8, more preferably at least 9.

The alkaline earth metal thiocarbonates (like the ammonium and alkali metal analogues) decompose upon exposure to the atmosphere, at ambient temperatures and humidities, to carbon disulfide. Therefore, the aqueous solution thereof will yield (upon evaporation of the water) a solvated alkaline earth metal thiocarbonate which decomposes to carbon disulfide, in the presence of atmospheric gases at ambient temperatures.

The aqueous solutions of alkaline earth thiocarbonates utilized in the method of this invention are stable to significant increases in vapor pressure, and significant solid phase formation, during storage periods. These solutions also maintain acceptable chemical stability during such periods, as measured by their ability to decompose to carbon disulfide upon application as a fumigant.

Soil application of these solutions can be accomplished either prior to planting or after plant growth is established. It should be noted, however, that different plant species exhibit differing tolerances to chemical agents. In addition, phytotoxicity to a particular plant can be dependent upon its growth stage. Germination is not inhibited for most plant seeds after soil treatment, and growth of established plants is not significantly altered. Some seedlings, though, show phytotoxicity symptoms to carbon disulfide. Postplant applications of the composition to such diverse crops as corn, cotton, tomatoes, potatoes and grapes give no indications of phytotoxicity at effective nematocidal application rates, but cucumber plants may be somewhat more sensitive to the composition.

The above solutions can be applied without further dilution (to minimize the amount which is required per acre) by spraying onto the soil surface, preferably followed within several hours by water application to move the composition into the soil before a significant amount of free carbon disulfide is released. Injection into the soil, using a shank or knife, is also a useful method for applying the composition. This application can either be "flat", wherein the injectors are closely spaced to treat essentially the entire field area, or can be "localized" by spacing the injectors such that only the plant growing bed is treated in bands.

Alternatively, the solutions can be mixed into irrigation water and applied by any customary manner, such as through sprinklers, in furrow or flood irrigation, and in drip irrigation systems. The dissolved alkaline earth metal thiocarbonate will move into the soil with the water, and decompose to accomplish its fumigation and nitrification inhibition functions.

The solutions also can be used in nonsoil fumigation procedures, such as in the chamber fumigation of commodities which are introduced into commerce. In this type of procedure, the application of heat can be used to promote a rapid decomposition into carbon disulfide. Upon termination of the fumigation procedure, vapors in the chamber can be drawn through a scrubbing system, e.g., one containing an alkaline aqueous solution, to remove the fumigant and prevent atmospheric pollution when the chamber is opened.

Another important use of the solutions is as a fumigant for stored grains and other agricultural products. If applied to products which are to be stored, the solution can be applied simply by spraying into the product as it is being transported to the storage enclosure with a conveyor, auger or other device. The solutions can also be applied to agricultural products which are already in storage, by spraying onto the exposed products and sealing the storage enclosure.

It is also possible to use the solutions for fumigating rooms or storage enclosures; this is accomplished by spraying the floor and walls therewith, and sealing the space until the desired fumigation is accomplished. As an alternative to spraying, a technique similar to chamber fumigation can be used, wherein heat decomposes the alkaline earth metal thiocarbonate in an enclosed space.

The fumigating ability of compositions described herein has been expressed primarily in terms of the available carbon disulfide content. It should be noted, however, that other components that may be generated upon decomposition of the alkaline earth metal thiocarbonate can contribute to efficacy as a fumigant. For example, sulfur is very widely used as a fungicide-acaricide-insecticide, so that the decomposition of the tetrathiocarbonates to form sulfur will have biocidal properties in addition to the properties attributable to the carbon disulfide content.

Upon heating or introduction into the soil, the alkaline earth metal thiocarbonates break down into their components by a process which can be conceptualized as a physical dissociation. In a soil environment, the alkaline earth metal cations are rapidly withdrawn into soil particles, and thereby rendered more or less immobile, depending upon soil characteristics, moisture conditions, ambient temperature and the like. Thus, the alkaline earth metal cations are available as micronutrients. Sulfur and hydrogen sulfide may be fixed by the soil and are available for oxidation to acidic sulfur oxides, which are useful to neutralize alkaline soils. Carbon disulfide, however, is not tightly bound to the soil and readily migrates to perform the fumigation function.

The alkaline earth metal thiocarbonates may be combined with other agricultural chemicals to provide a multifunctional product. For example, the stable salts may be combined with solid fertilizers such as urea, ammoniumnitrate, calcium nitrate, etc. and other sources of fertilizer nitrogen.

The invention is further illustrated by the following examples which are illustrative of various aspects of the invention, and are not intended as limiting the scope of the invention as defined by the appended claims.

EXAMPLE 1

The calcium tetrathiocarbonate utilized in the following examples is prepared as follows:

Calcium oxide (115.8 g, 2.1 mol) is slurried in 585 g of water. With good mixing, hydrogen sulfide (71.6 g, 2.1 mol) is bubbled in. To the resulting dark green slurry is added sulfur (67.4 g, 2.1 mol), which produces, with stirring, a dark yellow slurry. Carbon disulfide (180.69, 2.1 mol) is added to produce a deep yellow solution.

This reaction may be carried out with moderate cooling, or on a small scale, with no cooling. Air must be excluded to prevent the formation of unwanted oxidation products.

The reaction takes place equally well when sodium, potassium, cesium, strontium, or barium are used in proper molar ratios, in place of calcium. The hydroxides may be used, rather than the oxides, and elemental sulfur may be omitted when the trithiocarbonate is desired.

When any of these salts are added to soil, there is a quantitative breakdown to the original components. This can be monitored by analyzing the vapor space above the soil for carbon disulfide. In a very dry sandy loam soil, the rate of breakdown is very rapid, with maximum carbon disulfide appearing within two hours. The rate is slower in moist soil.

Solutions of these salts have efficacy against nematodes in approximate proportion to their equivalent carbon disulfide content.

EXAMPLE 2

The utility as nematocides for compositions of this invention is demonstrated in a greenhouse experiment with tomato plants.

In the experiment, thirty containers are used, each containing about 500 grams of sterilized sandy loam soil. Each container contains one tomato plant. Each container is injected with four 5-milliliter portions of extract from nematode-infested pepper roots, one inch below the soil surface, producing an initial population of 2000 root-knot nematode larvae (species *Meloidogyne incognita*) per container.

Ten treatments are replicated three times, each treatment consisting of drenching the soil with a solution containing the fumigant to provide the dosage of $CS_2$ given in Table 1. The solutions are diluted with sufficient water to saturate the soil. The treatments include calcium tetrathiocarbonate, ammonium tetrathiocarbonate, and carbon disulfide at three levels, plus an untreated control. After drenching, each container is allowed to stand at ambient conditions. The plants are harvested after 30 days of growth, and soil is removed from the roots by a gentle washing with water. By use of a magnifying glass, the number of root galls is counted on each plant.

Results are summarized in Table 1 in which the "Application" represents milligrams of treatment per kilogram of soil, calculated as the thiocarbonate salt and the equivalent carbon disulfide. Gall counts are mean values from the three replicates.

TABLE 1

| | | Dose, ppm | | Gall Counts[b] | | | |
|---|---|---|---|---|---|---|---|
| | | Application[a] Salt | Application Eq. $CS_2$ | 1 | 2 | 3 | Mean |
| (A) | Control | 0 | 0 | 4 | 7 | 1 | 4.0 |
| (B) | Ammonium Tetrathiocarbonate | 213 | 30 | 5 | 7 | 3 | 5.0 |
| (C) | Ammonium Tetrathiocarbonate | 425 | 60 | 9 | 15 | 6 | 10.0 |
| (D) | Ammonium Tetrathiocarbonate | 638 | 89 | 6 | 5 | 2 | 4.3 |
| (E) | Calcium Tetrathiocarbonate | 245 | 31 | 16 | 8 | 23 | 15.7 |
| (F) | Calcium Tetrathiocarbonate | 490 | 61 | 11 | 4 | 7 | 7.3 |
| (G) | Calcium Tetrathiocarbonate | 730 | 91 | 3 | 9 | 9 | 7.0 |
| (H) | $CS_2$ | — | 32 | 31 | 23 | 12 | 22.0 |
| (J) | $CS_2$ | — | 65 | 28 | 19 | 33 | 26.7 |
| (K) | $CS_2$ | — | 97 | 27 | 24 | 9 | 20.0 |

[a] $NH_4CS_4$ applied as a 32.4 percent solution, by weight.
$CaCS_4$ applied as a 29.6 percent solution, by weight.
$CS_2$ applied as the pure liquid.
[b] Number of discrete galls per total root mass.

The calcium tetrathiocarbonate is substantially equivalent to the ammonium tetrathiocarbonate as a nematocide; however, the calcium thiocarbonates (as well as the other alkaline earth metal thiocarbonates) are found to be less phytotoxic in that they do not form ammonium thiocyanate upon decomposition during storage, nor, unlike the ammonium ion component of the ammonium thiocarbonates, are the individual components, of the alkaline earth metal thiocarbonates (i.e., $H_2S$, S, $CS_2$, and alkaline earth metal ions), phytotoxic.

EXAMPLE 3

The procedure of Example 2 is repeated except that potassium tetrathiocarbonate is substituted for ammonium tetrathiocarbonate and an in-vitro nematocidal test is used. In the in-vitro test, the nematode larvae are treated in aqueous suspension for 1 hour at the concentrations of fumigant given in Table 2, washed twice with water, and injected into the active root zone of the tomato plants. After thirty days the roots are harvested, examined for galling, and the results summarized in Table 2.

TABLE 2

| | | Gall Count | | |
|---|---|---|---|---|
| | Treatment | 1 | 2 | Mean |
| A | Control | 90 | 88 | 89 |
| B | 50 ppm calcium tetrathiocarbonate 6.3 ppm $CS_2$ equiv. | 185 | 149 | 167 |
| C | 100 ppm calcium tetrathiocarbonate 12.5 ppm $CS_2$ equiv. | 132 | 184 | 158 |
| D | 150 ppm calcium tetrathiocarbonate 18.8 ppm $CS_2$ equiv. | 32 | 66 | 49 |
| E | 50 ppm Potassium tetrathiocarbonate 6.5 ppm $CS_2$ equiv. | 33 | 66 | 49.5 |
| F | 100 ppm Potassium tetrathiocarbonate 13 ppm $CS_2$ equiv. | 198 | 145 | 171.5 |
| G | 150 ppm Potassium tetrathiocarbonate 19.5 ppm $CS_2$ equiv. | 49 | 22 | 35.5 |
| H | 6 ppm Vydate TM (a) | 34 | 147 | 90.5 |
| J | 10 ppm $CS_2$ | 64 | 149 | 106.5 |
| K | 20 ppm $CS_2$ | 29 | 73 | 51.0 |

(a) duPont's trademark for oxamyl, a commercial nematocide.

The results show that the calcium tetrathiocarbonate is substantially equivalent to potassium tetrathiocarbonate as a nematocide. However, as described below, the potassium thiocarbonates are less stable to storage as measured by the loss of their ability to generate the active fumigant carbon disulfide.

EXAMPLE 4

Various tetrathiocarbonate salts are evaluated for storage stability by measuring the loss of the ability of aqueous solutions thereof to generate carbon disulfide upon contact with strong acid. Aqueous solutions of the salts listed in Table 3, below, having an equivalent of from about 14 to about 16 percent, by weight, carbon disulfide, are stored in air-tight glass containers at a temperature of 120° F. As shown by the data in Table 3, the calcium tetrathiocaronate solution is significantly more stable than the sodium and potassium tetrathiocarbonate solutions and substantially more stable than the ammonium tetrathiocarbonate.

TABLE 3

| Cation | Half-life (months) |
|---|---|
| $NH_4$ | 0.17 |
| Na | 3.0 |
| K | 2.9 |
| Ca | 5.0 |

EXAMPLE 5

Aqueous solutions of alkali metal or alkaline earth metal tri- or tetrathiocarbonates have very high solvency for urea, indicating that eutectic compositions are formed. These combinations are biocidal against bacteria, fungi, nematodes, and insects, while providing a wide range of desirable nitrogen and sulfur fertilizer contents. Furthermore, alkali metal and alkaline earth metal cations, in particular, calcium, magnesium, and potassium, are indispensable plant nutrients. Thus, the compositions described above may be used to provide the major nutrient requirements of crops, while at the same time protecting the crops against pathogens.

To a 41.5 percent, by weight, aqueous solution of calcium tetrathiocarbonate is added urea until the solubility limit of urea is reached. At room temperature, the solution dissolves 122 percent by weight urea. The resulting solution is 55 percent urea, 18.6 percent calcium tetrathiocarbonate, and 26.3 percent water, by weight. Thus, the solvency of the aqueous solution of calcium tetrathiocarbonate for urea is at least as great as that of water alone. Similarly, a 46 percent solution of potassium tetrathiocarbonate dissolves 100 percent of its own weight of urea. Similar results obtain with other tri- and tetrathiocarbonates of alkali metal and alkaline earth metals.

EXAMPLE 6

It has been found, that the stability of dilute aqueous solutions of alkaline earth metal thiocarbonates (as measured by rate of decomposition to yield carbon disulfide increases with the pH of the solution. Therefore, in irrigation applications, wherein dilute solutions are utilized, it is desirable to provide a base to increase the pH of the irrigation solution. A suitable base may be selected from the group consisting of the alkali metal hydroxides and carbonates, e.g. KOH, NaOH, $K_2CO_3$, $Na_2CO_3$, etc. The base may be added to the water of dilution utilized in making up the irrigation solution or can be incorporated in the aqueous alkaline earth metal thiocarbonate solution. Sufficient base is added to provide an irrigation solution having a pH of at least about 7 and preferably at least about 8.0. Most preferably, the amount of base added will provide an irrigation solution having a pH of at least about 9.0.

In this example, an aqueous solution comprising 29.6 percent by weight $CaCS_4$ is diluted to 400 mg per liter with ambient water to which has been added sufficient base, e.g. NaOH, to provide a solution having the pH given below. The solutions are placed in sealed containers and the concentration of $CS_2$ in the vapor space above the solution is measured with time. As shown, the $CaCS_4$ in the control solution (no added base) decomposes within 1 minute to release substantially all of the combined $CS_2$. The solutions that have sufficient base to provide a pH of 7.0, 8.0 and 9.0 decompose more slowly to $CS_2$, with the rate of decomposition decreasing with increasing pH. The results are summarized in Table 4, below:

TABLE 4

| Solution pH | Time, min | $CS_2$ Vapor, Mol % | $t_{\frac{1}{2}}$, min |
|---|---|---|---|
| 5.2 (control) | 1.0 | 1.04 | <1 |
|  | 5.0 | 1.05 |  |
|  | 9.0 | 1.05 |  |
| 6.0 | 1.0 | 0.89 | <1 |
|  | 5.5 | 0.89 |  |
|  | 9.8 | 0.92 |  |
|  | 21.0 | 0.96 |  |
|  | 28.0 | 0.91 |  |
| 7.0 | 1.0 | 0.20 | 2.1 |
|  | 5.5 | 0.96 |  |
|  | 9.0 | 1.02 |  |
|  | 14.0 | 1.02 |  |
| 8.0 | 1.0 | 0.02 | 9.2 |
|  | 5.0 | 0.23 |  |
|  | 9.0 | 0.53 |  |
|  | 14.0 | 0.82 |  |
|  | 18.0 | 0.94 |  |
|  | 29.0 | 1.01 |  |
|  | 34.0 | 1.02 |  |
| 9.0 | 1.0 | 0.03 | 26.1 |
|  | 5.5 | 0.15 |  |
|  | 9.0 | 0.26 |  |
|  | 15.5 | 0.42 |  |
|  | 23.0 | 0.58 |  |
|  | 30.0 | 0.69 |  |
|  | 40.0 | 0.80 |  |
|  | 50.0 | 0.88 |  |
|  | 60.0 | 0.89 |  |
|  | 80.0 | 0.96 |  |
|  | 100.0 | 0.98 |  |

While particular embodiments of the invention have been described it will be understood of course that the invention is not limited thereto since many obvious modifications can be made and it is intended to include within this invention any such modifications as will fall within the scope of the appended claims.

Having now described the invention,

I claim:

1. An aqueous solution comprising (1) a thiocarbonate selected from the group consisting of alkali and alkaline earth metal thiocarbonates, and combinations thereof dissolved in a quantity of water, and (2) an amount of urea, dissolved in said solution, greater than the solubility limit of urea in said quantity of water.

2. The composition defined in claim 1, wherein said thiocarbonate comprises a member selected from the group consisting of alkali and alkaline earth metal tetrathiocarbonates and combinations thereof.

3. The composition defined in claim 1, wherein said thiocarbonate comprises a member selected from the group consisting of calcium and potassium tetrathiocarbonates and combinations thereof.

4. The composition defined in claim 1, wherein said solution consists essentially of said thiocarbonate, water, and urea.

5. An aqueous solution comprising urea, a thiocarbonate compound selected from the group consisting of alkali and alkaline earth metal thiocarbonates and combinations thereof, and a quantity of water, wherein the combined concentration of dissolved urea and thiocarbonate is greater than that which could dissolve in said quantity of water were said solution an ideal solution.

6. The composition defined in claim 5, wherein said thiocarbonate compound comprises a member selected from the group consisting of alkali and alkaline earth metal tetrathiocarbonates and combinations thereof.

7. The composition defined in claim 5 consisting essentially of said urea, thiocarbonate compound, and water.

8. A method for fumigating soil which comprises applying to the soil a fumigating effective amount of the composition defined in claim 1.

9. A method for fumigating soil which comprises applying to the soil a fumigating effective amount of the composition defined in claim 5.

10. A fumigation method comprising applying to the vicinity to be fumigated a fumigating effective amount of the composition defined in claim 1.

11. A fumigation method comprising applying to the vicinity to be fumigated a fumigating effective amount of the composition defined in claim 5.

12. A fertilization method comprising applying to soil a fertilizing effective amount of the composition defined in claim 1.

13. A fertilization method comprising applying to soil a fertilizing effective amount of the composition defined in claim 5.

14. The composition consisting essentially of a thiocarbonate selected from the group consisting of alkali and alkaline earth metal thiocarbonates and combinations thereof, urea, and a quantity of water, wherein the combined concentration of dissolved urea and thiocarbonate is greater than that which could dissolve in said quantity of water were said solution an ideal solution.

15. The composition defined in claim 14, wherein said thiocarbonate comprises a member selected from the group consisting of alkali and alkaline earth metal tri- and tetrathiocarbonates and combinations thereof.

16. The composition defined in claim 14, wherein said thiocarbonate comprises a member selected from the group consisting of alkali and alkaline earth metal tetrathiocarbonates and the combinations thereof.

17. The composition defined in claim 14, wherein said thiocarbonate comprises a member selected from the group consisting of calcium and potassium tetrathiocarbonates and combinations thereof.

18. A fumigation method comprising applying to the vicinity to be fumigated a fumigating effective amount of the composition defined in claim 14.

19. A fertilization method comprising applying to soil a fertilizing effective amount of the composition defined in claim 14.

20. A method for controlling pests selected from the group consisting of bacteria, fungi, insects, rodents, nematodes, and combinations thereof, which comprises applying to the vicinity occupied by said pests an amount of the composition defined in claim 1 sufficient to control said pests.

21. A method for controlling pests selected from the group consisting of bacteria, fungi, insects, rodents, nematodes, and combinations thereof, which comprises applying to the vicinity occupied by said pests an amount of the composition defined in claim 5 sufficient to control said pests.

22. A method for controlling pests selected from the group consisting of bacteria, fungi, insects, rodents, nematodes, and combinations thereof, which comprises applying to the vicinity occupied by said pests an amount of the composition defined in claim 14 sufficient to control said pests.

* * * * *